United States Patent [19]
Audia et al.

[11] Patent Number: 5,631,265
[45] Date of Patent: May 20, 1997

[54] 8-SUBSTITUTED TETRAHYDRO-BETA-CARBOLINES

[75] Inventors: James E. Audia; James J. Droste; Jeffrey S. Nissen, all of Indianapolis, Ind.

[73] Assignee: Eli Lilly and Company, Indianapolis, Ind.

[21] Appl. No.: 380,564

[22] Filed: Feb. 6, 1995

Related U.S. Application Data

[63] Continuation-in-part of Ser. No. 358,644, Dec. 19, 1994, abandoned, which is a continuation of Ser. No. 212,404, Mar. 11, 1994, abandoned.

[51] Int. Cl.$^6$ .................... A61K 31/395; C07D 471/04
[52] U.S. Cl. .................... 514/292; 546/85; 546/86; 546/87
[58] Field of Search .................... 514/292; 546/85, 546/86, 87

[56] References Cited

U.S. PATENT DOCUMENTS

| | | | |
|---|---|---|---|
| 3,071,589 | 1/1963 | Archer | 260/296 |
| 3,304,309 | 2/1967 | Shavel et al. | 260/296 |
| 3,455,943 | 7/1969 | Remers et al. | 260/296 |
| 3,492,304 | 1/1970 | Shavel et al. | 260/288 |
| 3,718,657 | 2/1973 | Garmaise et al. | 260/296 A |
| 4,978,669 | 12/1990 | Barchas et al. | 514/292 |

FOREIGN PATENT DOCUMENTS 17727 10/1980 European Pat. Off. .............. 514/292

OTHER PUBLICATIONS

Chem. Abstract, "109 (11):93404s", vol. 109, p. 751 (1988).
Chem. Abstracts, "83(13):114719k", vol. 83, p. 591 (1975).
Chem. Abstracts, "72(19):100674c", vol. 72, p. 374 (1970).
Chem. Abstracts, "77(25):164922t", vol. 77, (1972).
Chem. Abstracts, "94(11):84091g", vol. 94, p. 726 (1981).
Chem. Abstracts, "111(23):208701x", vol. 111, (1989).
Chem. Abstracts, "90(25):203905e", vol. 90, p. 609 (1979).
Chem. Abstracts, "94(3):15940w", vol. 94, p. 465 (1981).
Chem. Abstracts, "66(21):95019n", vol. 66, p. 890 (1967).
Chem. Abstracts, "88(21):145971u", vol. 88, p. 22 (1978).
Chem. Abstracts, "78(19):124791p", vol. 78, p. 505 (1973).
Derwent Publications, "J56045-459", Otsuka Pharm KK, filed Sep. 20, 1979, published Apr. 25, 1981.
Derwent Publications, "J55133-360", Shonot, filed Apr. 3, 1979, published Oct. 17, 1980.
Derwent Publications, "J50077-396", Nippon Chemifar, filed Nov. 13, 1973, published Jun. 24, 1975.
Derwent Publications, "J50024-299", Nippon Chemifar, filed Jun. 28, 1973, published Mar. 15, 1975.
Derwent Publications, "26,841", Upjohn Co., filed Jun. 11, 1963, published Jun. 1, 1967.
A. R. Stoit, et al., *Heterocycles* 22(8), 1687–91 (1984).
Shono et al., *J. Org. Chem.*, 48:1621–1628 (1983).
Liu et al., *J. Org. Chem.*, 48(1) 44–47 (1983).
Hudlicky et al., *J. Org. Chem.*, 46:1738–1741 (1981).
*J. Org. Chem.*, 47:2229–2231 (1982).
Chem. Abstracts, "90(5):34483b", vol. 113, p. 25 (1990).
Chem. Abstracts, (Organic Chemistry) 4666 citing *Chem. Listy* 51, 1915–22 (1957).
Chem. Abstrcts, vol. 52:11039 citing *Monatsh. Chem.* 88, 1087–94 (1958).
Chem. Abstracts, vol. 54:1584 citing *Czech.* 86, 787 (1957).
Chem. Abstracts, vol. 55:21156 citing *Bull. Soc. Chim. France*, 643–653 (1960).
Bojarski, A.J. et al., *Pharmazie* 48:289–294 (1993).
Abandoned application 08/206,839 of Aliz et al. (1993).

*Primary Examiner*—Joseph E. Evans
*Attorney, Agent, or Firm*—MaCharri Vorndran-Jones; David E. Boone

[57] ABSTRACT

The present invention provides novel tetrahydro-beta-carboline compounds and intermediates having useful central nervous system activity. The invention provides formulations and methods for using the tetrahydro-beta-carboline and related intermediate compounds. Finally, the invention provides an article of manufacture.

25 Claims, No Drawings

8-SUBSTITUTED TETRAHYDRO-BETA-CARBOLINES

CROSS REFERENCE

This application is a continuation-in-part of Ser. No. 08/358,644 filed on Dec. 19, 1994, now abandoned, which is a continuation of Ser. No. 08/212,404 filed on Mar. 11, 1994, now abandoned.

FIELD OF THE INVENTION

The present invention relates to the field of organic chemistry. The invention provides novel 8-substituted tetrahydro-beta-carboline compounds and intermediates with a high affinity for the 5-$HT_2$ receptors.

BACKGROUND OF THE INVENTION

A substantial body of evidence supports the relationship between 5-$HT_2$ receptor modulation and a variety of diseases and conditions. The 5$HT_2$ receptor class, as used herein, generically includes 5-$HT_{2A}$, 5-$HT_{2B}$, and/or 5-$HT_{2C}$ receptors. The specific 5-$HT_2$ receptor subtypes are named when a specific subtype is intended.

The activation of the 5-$HT_2$ receptor has been associated with numerous behavioral and physiological effects. TiPS, 11, 181 (May 1990). The 5$HT_2$ receptors in the limbic system can affect mood, behavior, and hallucinogenesis. Hartig et al., The 5-$HT_{1C}$ Receptor *Annals New York Academy of Science*, 149, 159. Modulation of the 5$HT_2$ receptors has been associated with schizophrenia and schizophreniform disorders. Ugedo, L. et al. *Psychopharmacology*, 98, 45 (1989); Canton H. et al. *Eur. J. Pharmacol.*, 191, 93 (1990). Hypothalamic 5-$HT_2$ receptors can influence sleep, appetite, thermoregulation, sexual behavior, motor activity, and neuroendocrine function. Hartig et al., The 5-$HT_{1C}$ Receptor *Annals New York Academy of Science*, 149, 159. Additionally, studies indicate that 5-$HT_2$ receptors mediate hypoactivity, caused decreased feeding in rats, and have anxiogenic effects. Id. Studies have shown that drug-induced penile erections are 5-$HT_2$ mediated. *Psychopharmacology*, 101, 57 (1990). Likewise, 5-$HT_2$ modulation can treat or prevent priapism.

Studies evince that 5-$HT_2$ receptors influence the onset of anxiety, obsessive-compulsive disorders, panic disorders, Gilles de la Tourette syndrome and migraine headaches. TiPS, 11, 181 (May 1990). The studies indicate that the 5-$HT_2$ receptor can be involved in Alzheimer's disease as well. Id. The 5-$HT_2$ receptor is involved in the modulation of the balance of cerebrospinal fluid. Further, the 5-$HT_2$ receptor is associated with the sensation of pain. Zemlan, F. P. et al. *Neurochem, Int.*, 16, 507 (1990).

Further, compounds having affinity and selectivity for the 5$HT_2$ receptor can be useful for treating a variety of conditions related to 5$HT_{2A}$, 5$HT_{2B}$, and/or 5$HT_{2C}$ modulation. For example, compounds useful for the modulation of the 5$HT_{2B}$ receptor are useful for treating patients suffering from or susceptible to ichlasia, hypertonic lower esophogeal sphincter, tachygastria, hypermotility associated with irritable bowel syndrome, constipation, dyspepsia, and other 5-$HT_{2B}$ related conditions. Additionally, modulation of the 5$HT_2$A receptor has been associated with schizophrenia, anxiety, depression, and migraines. Koek, W. *Neuroscience and Biobehavioral Reviews*, 16, 95–105 (1992).

It would be advantageous to have compounds which would permit modulation of the 5-$HT_{2A}$, 5$HT_{2B}$, and/or 5$HT_{2C}$ receptors. It would be particularly desirable to have compounds with high 5-$HT_2$ receptor subtype affinity and selectivity. It would be further advantageous to have compounds that minimize the effects of eating disorders, sexual disorders, and other disorders or conditions associated with 5-$HT_2$ receptor subtype modulation.

SUMMARY OF THE INVENTION

This invention provides a group of novel compounds with 5-$HT_2$ receptor activity. The invention also provides compounds with desired selective 5-$HT_{2A}$ and 5-$HT_{2C}$ receptor activity. Additionally, the present compounds are useful tools to characterize the effects of the 5-$HT_2$ receptor and to develop therapeutic agents based on 5-$HT_2$ receptor and 5$HT_2$ receptor subtype modulation.

Thus, this invention relates to a compound of the Formula I

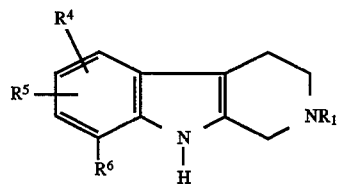

wherein:

$R^1$ is hydrogen, $C_1$–$C_3$ alkyl, substituted $C_3$–$C_8$ cycloalkyl, $C_3$–$C_8$ cycloalkyl, $C_3$–$C_8$ cycloalkyl-($C_1$–$C_3$) alkyl, $C_5$–$C_8$ cycloalkenyl-($C_1$–$C_3$)alkyl, or $C_7$–$C_{16}$ arylalkyl;

$R^4$ and $R^5$ are independently hydrogen, $C_1$–$C_3$ alkyl, $C_2$–$C_6$ alkenyl, halo, halo($C_1$–$C_6$)alkyl, halo($C_2$–$C_6$) alkenyl, $COR^7$, $C_1$–$C_{10}$ alkanoyl, $CO_2R^{7'}$, ($C_1$–$C_6$ alkyl)$_m$ amino, $NO_2$, —$SR^7$, $OR^7$, substituted $C_3$–$C_8$ cycloalkyl, $C_3$–$C_8$ cycloalkyl, $C_3$–$C_8$ cycloalkyl-($C_1$–$C_3$) alkyl, $C_5$–$C_8$ cycloalkenyl-($C_1$–$C_3$) alkyl, or $C_7$–$C_{16}$ arylalkyl;

m is 1 or 2;

each $R^7$ is independently hydrogen or $C_1$–$C_4$ alkyl;

$R^{7'}$ is $C_1$–$C_4$ alkyl;

$R^6$ is selected from the group consisting of $C_1$–$C_4$ alkyl, $OR^{5'}$, fluoro, bromo, iodo, and chloro;

$R^{5'}$ is selected from the group consisting of hydrogen and $C_1$–$C_4$ alkyl; or a pharmaceutically acceptable salt or solvate thereof.

The present invention also provides methods of employing and pharmaceutical formulations containing, a compound of formula I or a pharmaceutically acceptable salt or solvate thereof.

A further embodiment of this invention is an article of manufacture comprising packaging material and one or more pharmaceutical agents contained within said packaging material, wherein said pharmaceutical agent is effective for the treatment of a condition associated with 5-$HT_{2C}$ modulation and is a compound of Formula I; or a pharmaceutically acceptable salt or solvate thereof; and said packaging material comprises a label which indicates that said pharmaceutical agent can be used for the treatment of a condition associated with 5-$HT_{2C}$ modulation.

DETAILED DESCRIPTION OF THE INVENTION

As used herein the term "5$HT_2$" receptor includes 5-$HT_{2A}$, 5-$HT_{2B}$, and 5-$HT_{2C}$ receptor subtypes unless a specific subtype is named.

The term "treating" as used herein includes prophylaxis of the named physical and/or mental condition or amelioration or elimination of the developed physical and/or mental condition once it has been established.

The phrase "injury to the central nervous system" includes, but is not limited to, injury to the spinal cord, neural tube, or dura of the brain. Injury to the central nervous system also includes priapism, cerebrospinal fluid imbalances, and other $5\text{-}HT_{2A}$, $5\text{-}HT_{2B}$, and $5\text{-}HT_{2C}$ imbalances, and related conditions resulting from central nervous system injury.

The terms "$C_1\text{-}C_n$ alkyl" wherein n=2–10, as used herein, represent a branched or linear alkyl group having from one to the specified number of carbon atoms. Typical $C_1\text{-}C_6$ alkyl groups include methyl, ethyl, n-propyl, iso-propyl, butyl, iso-butyl, sec-butyl, tert-butyl, pentyl, hexyl and the like.

The terms "$C_2\text{-}C_n$ alkenyl" wherein n=3–10, as used herein, represents an olefinically unsaturated branched or linear group having from 2 to 10 carbon atoms and at least one double bond. The groups can be branched or straight chain. Examples of such groups include 1-propenyl, 2-propenyl ($-CH_2-CH=CH_2$), 1,3-butadienyl ($-CH=CHCH=CH_2$), 1-butenyl ($-CH=CHCH_2CH_3$), hexenyl, pentenyl, and the like.

The terms "halide", "halogen", and "halo" include fluorine, chlorine, bromine, and iodine. The preferred halogen is chlorine.

The terms "halo($C_1\text{-}C_6$)alkyl" and "halo($C_2\text{-}C_6$)alkenyl" refer to alkyl or alkenyl substituents having one or more independently selected halo atoms attached at one or more available carbon atoms. These terms include chloromethyl, bromoethyl, trifluoroethyl, trifluoromethyl, trifluoroethylenyl, 3-bromopropyl, 3-bromo-1-propenyl, 2-bromopropyl, 2-bromo-1-propenyl, 3-chlorobutyl, 3-chloro-2-butenyl, 2,3-dichlorobutyl, chloroethylenyl, 5-fluoro-3-penyenyl, 3-chloro-2-bromo-5-hexenyl, 3-chloro-2-bromo-butyl, trichloromethyl, dichloroethyl, 1,4-dichlorobutyl, 3-bromopentyl, 1,3-dichlorobutyl, 1,1-dichloropropyl, and the like. More preferred halo-($C_1\text{-}C_6$) alkyl groups are trichloromethyl, trichloroethyl, and trifluoromethyl. The most preferred halo-($C_1\text{-}C_6$)alkyl is trifluoromethyl.

The term "$C_1\text{-}C_{10}$ alkanoyl" represents a group of the formula $C(O)(C_1\text{-}C_9)$ alkyl. Typical $C_1\text{-}C_{10}$ alkanoyl groups include acetyl, propanoyl, butanoyl, and the like.

The term "($C_1\text{-}C_6$ alkyl)$_m$amino" wherein m=1–2; refers to either a mono- or a dialkylamino group in which the alkyl portion of the group may be straight or branched. Examples of such groups are methylamino, dimethylamino, ethylamino, diethylamino, 2-propylamino, 1-propylamino, di(n-propyl)amino, di(iso-propyl)amino, methyl-n-propylamino, t-butylamino, and the like.

The term "$C_3\text{-}C_n$ cycloalkyl" wherein n=4–8, represents cyclopropyl, cyclobutyl, cyclopentyl, cyclohexyl, cycloheptyl, and cyclooctyl.

The term "substituted ($C_5\text{-}C_n$) cycloalkyl" refers to a cycloalkyl group as described supra wherein the cycloalkyl group may be substituted with from one to four substituents independently selected from the group consisting of hydrogen, $C_1\text{-}C_6$ alkyl, $NO_2$, halo, halo($C_1\text{-}C_6$)alkyl, halo ($C_2\text{-}C_6$)alkenyl, $C_2\text{-}C_6$ alkenyl, $CO_2R_5$, ($C_1\text{-}C_6$ alkyl)$_m$amino, $-SR_5$, and $OR_5$.

The term "$C_3\text{-}C_8$ cycloalkyl-($C_1\text{-}C_3$)alkyl" represents a linear alkyl group substituted at a terminal carbon with a $C_3\text{-}C_8$ cycloalkyl group. Typical cycloalkylalkyl groups include cyclohexylethyl, cyclohexylmethyl, 3-cyclopentylpropyl, and the like.

The term "$C_5\text{-}C_8$ cycloalkenyl" represents an olefinically unsaturated ring having five to eight carbon atoms, e.g., phenyl, cyclohexadienyl, cyclohexenyl, cyclopentenyl, cycloheptenyl, cyclooctenyl, cyclohexadienyl, cycloheptadienyl, cyclooctatrienyl and the like.

The term "substituted ($C_5\text{-}C_8$) cycloalkenyl" refers to a cycloalkenyl group as described supra wherein the cycloalkenyl group may be substituted with from one to four substituents independently selected from the group consisting of hydrogen, $C_1\text{-}C_6$ alkyl, $NO_2$, halo, halo ($C_1\text{-}C_6$)alkyl, halo($C_2\text{-}C_6$)alkenyl, $C_2\text{-}C_6$ alkenyl, $COR_5$, $C_1\text{-}C_{10}$ alkanoyl, $C_7\text{-}C_{16}$ arylalkyl, $CO_2R_5$, ($C_1\text{-}C_6$ alkyl)$_m$amino, $-SR_5$, and $OR_5$.

The term "$C_5\text{-}C_8$ cycloalkenyl-($C_1\text{-}C_3$)alkyl" represents a linear $C_1\text{-}C_3$ alkyl group substituted at a terminal carbon with a $C_5\text{-}C_8$ cycloalkenyl group.

The term "aryl" represents phenyl or naphthyl. The aryl group can be unsubstituted or can have one or two substituents independently selected from the group consisting of $C_1\text{-}C_6$ alkyl, $C_3\text{-}C_8$ cycloalkyl, substituted $C_3\text{-}C_8$ cycloalkyl, $C_2\text{-}C_6$ alkenyl, $C_3\text{-}C_8$ cycloalkyl-($C_1\text{-}C_3$)alkyl, phenyl, $C_5\text{-}C_8$ cycloalkenyl, substituted $C_5\text{-}C_8$ cycloalkenyl, $C_5\text{-}C_8$ cycloalkenyl-($C_1\text{-}C_3$)alkyl, $COR_5$, $C_1\text{-}C_{10}$ alkanoyl, $OR_5$, and $C_7\text{-}C_{16}$ arylalkyl. The substituents may be located at any available position on the aryl ring.

The term "$C_7\text{-}C_{16}$ arylalkyl" represents an aryl-($C_1\text{-}C_{10}$) alkyl substituent wherein the alkyl group is linear, such as benzyl, phenethyl, 3-phenylpropyl, or phenyl-t-butyl; or branched.

The term "selective binding of a $5\text{-}HT_{2A}$ receptor" refers to a method of binding the $5\text{-}HT_{2A}$ receptor to a greater extent than it binds the other $5\text{-}HT_2$ receptor subtypes. Likewise, certain compounds of this invention selectively bind a $5\text{-}HT_{2B}$ or $5\text{-}HT_{2C}$ receptor to a greater extent than it binds the other $5\text{-}HT_2$ subtypes.

The term "protic acid" refers to an acid having an acidic hydrogen. Preferred protic acids include hydrochloric acid, formic acid, perchloric acid, sulfuric acid, and phosphoric acid in an aqueous medium. The most preferred protic acids are hydrochloric acid, sulfuric acid, and formic acid.

The term "organic solvent" includes solvents containing carbon, such as halogenated hydrocarbons, ether, toluene, xylene, benzene, and tetrahydrofuran.

The term "agitate" includes such techniques as stirring, centrifugation, mixing, and other similar methods.

The term "aprotic solvent" refers to polar solvents of moderately high dielectric constant which do not contain an acidic hydrogen. Examples of common aprotic solvents are dimethyl sulfoxide (DMSO), dimethylformamide, sulfolane, tetrahydrofuran, diethyl ether, methyl-t-butyl ether, or 1,2-dimethoxyethane.

The term "protic solvent" refers to a solvent containing hydrogen that is attached to oxygen, and hence is appreciably acidic. Common protic solvents include such solvents as water, methanol, ethanol, 2-propanol, and 1-butanol.

The term "inert atmosphere" refers to reaction conditions in which the mixture is covered with a layer of inert gas such as nitrogen or argon.

Abbreviations used herein have their accepted meaning, unless stated otherwise. For example, "Me" and "Et" refer to methyl, ethyl respectively, and "t-Bu" refers to tertiary-butyl. The abbreviation "RT" refers to room temperature or ambient conditions unless indicated otherwise.

The term "ligand" refers to compounds that are bound by the $5\text{-}HT_2$ receptor. Compounds useful as $5\text{-}HT_2$ selective ligands may be used to selectively occupy the $5\text{-}HT_2$ receptor site or may act as a selective agonist at the $5\text{-}HT_2$ receptor site. Certain compounds are 5-HT$_{2A}$, 5-HT$_{2B}$, or 5-HT$_{2C}$ selective ligands.

The term "substantially pure" is intended to mean at least about 90 mole percent, more preferably at least about 95 mole percent, and most preferably at least about 98 mole percent of the desired enantiomer or stereoisomer is present compared to other possible configurations.

As used herein the term "functional bowel disorder" refers to a functional gastrointestinal disorder manifested by (1) abdominal pain and/or (2) symptoms of disturbed defecation (urgency, straining, feeling of incomplete evacuation, altered stool form [consistency] and altered bowel frequency/timing) and/or (3) bloating (distention). The term "functional bowel disorder" includes but is not limited to irritable bowel syndrome, hypermotility, ichlasia, hypertonic lower esophogeal sphincter, tachygastria, constipation, hypermotility associated with irritable bowel syndrome.

The artisan will recognize that compounds of Formula I are numbered as illustrated:

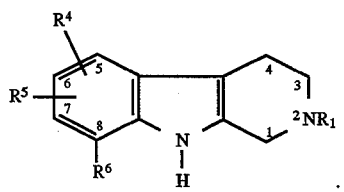

The Formula I and all compounds claimed herein can form acid addition salts with a wide variety of inorganic and organic acids. Typical acids which can be used include sulfuric, hydrochloric, hydrobromic, phosphoric, hypophosphoric, hydroiodic, sulfamic, citric, oxalic, acetic, maleic, malic, succinic, tartaric, cinnamic, benzoic, ascorbic, mandelic, p-toluenesulfonic, benzenesulfonic, methanesulfonic, trifluoroacetic, hippuric and the like. The pharmaceutically acceptable acid addition salts of the Formula I compounds are especially preferred.

Compounds of Formula I are useful for modulating 5HT$_2$ (including 5HT$_{2A}$, 5HT$_{2B}$, and/or 5HT$_{2C}$ receptors. Certain compounds within the scope of this invention are preferred for that use. The following invention embodiments and compound characteristics listed in tabular form may be independently combined to produce a variety of preferred compounds and embodiments of the invention. The following list of embodiments of this invention is in no way intended to limit the scope of this invention in any way.

A) $R^1$ is hydrogen;
B) $R^5$ is at the 6-position;
C) $R^6$ is fluoro, chloro, bromo, iodo, methoxy, ethoxy, or $C_1$–$C_4$ alkyl;
D) $R^4$ is $C_1$–$C_6$ alkyl, $C_5$–$C_8$ cycloalkyl, phenyl or substituted-phenyl;
E) $R^5$ is methoxy, hydroxy, or halo;
F) $R^5$ is chloro, methyl, or cycloalkyl;
G) $R^4$ is substituted $C_5$–$C_8$ cycloalkenyl; wherein the substituents are selected from the group consisting of hydrogen, NO$_2$, halo, ($C_1$–$C_6$ alkyl)$_m$amino, and OR$_5$;
H) $R^6$ is $C_1$–$C_4$ alkyl, fluoro, chloro, or bromo.
I) $R^6$ is —OCH$_3$.
J) $R^6$ is $C_1$–$C_4$ alkyl.
K) $R^6$ is methyl.
L) A method for binding a 5HT$_2$ receptor using one or more compounds of Formula I.
M) A method for binding a 5HT$_{2B}$ receptor using one or more compounds of Formula I.

N) A method for binding a 5HT$_{2C}$ receptor using one or more compounds of Formula I.
O) A method of using one or more compounds of Formula I for treating a functional bowel disorder.
P) A method of using one or more compounds of Formula I which are useful for modulatation of the 5HT$_{2B}$ receptor for treating a functional bowel disorder.
Q) A method for using one or more compounds of Formula I for treating Irritable Bowel Syndrome.
R) A pharmaceutical formulation comprising a compound of Formula I and one or more pharmaceutically acceptable excipients.
S) A compound wherein $R^6$ is halo.
T) A compound wherein $R^4$ and $R^5$ are each $C_1$–$C_3$ alkyl and $R^6$ is chloro or bromo.
U) A compound wherein $R^4$ and $R^5$ are each $C_3$–$C_8$ cycloalkyl or substituted $C_3$–$C_8$ cycloalkyl.
V) A compound wherein $R^1$ is selected from the group consisting of substituted $C_3$–$C_8$ cycloalkyl, $C_3$–$C_8$ cycloalkyl, $C_5$–$C_8$ cycloalkenyl-($C_1$–$C_3$)alkyl, and $C_7$–$C_{16}$ arylalkyl.
W) A compound wherein $R^1$ is selected from the group consisting of substituted $C_3$–$C_8$ cycloalkyl, $C_3$–$C_8$ cycloalkyl.
X) A compound wherein $R^1$ is hydrogen.
Y) A compound wherein $R^4$ and $R^5$ are independently selected from the group consisting of $C_2$–$C_6$ alkenyl, halo($C_1$–$C_6$)alkyl, halo($C_2$–$C_6$)alkenyl, COR$^7$, $C_1$–$C_{10}$ alkanoyl, CO$_2$R$^{7'}$, ($C_1$–$C_6$ alkyl)$_m$ amino, NO$_2$, —SR$^7$, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$) alkyl, or $C_7$–$C_{16}$ arylalkyl;
Z) A compound wherein $R^4$ and $R^5$ are independently selected from the group consisting of $C_1$–$C_{10}$ alkanoyl, CO$_2$R$^{7'}$, ($C_1$–$C_6$ alkyl)$_m$amino, NO$_2$, substituted $C_3$–$C_8$ cycloalkyl, $C_3$–$C_8$ cycloalkyl, $C_3$–$C_8$ cycloalkyl-($C_1$–$C_3$) alkyl, and $C_5$–$C_8$ cycloalkenyl-($C_1$–$C_3$)alkyl.
Z1) A compound wherein $R^1$ is hydrogen, $R^6$ is halo, $R^5$ and $R^6$ are selected from the group consisting of hydrogen, halo, and cycloalkyl.

Especially preferred invention embodiments have the following features:

A–D, H, L, O, and R.

The Formula I compounds have useful central nervous system activity. Examples of compounds of Formula I include but are in no way limited to 7-bromo-8-methyl-1,2,3,4-tetrahydro-9H-pyrido[3,4b]-indole, 6-isopropyl-8-methoxy-1,2,3,4-tetrahydro-9H-pyrido[3,4b]-indole, 5-chloro-8-ethoxy-1,2,3,4-tetrahydro-9H-pyrido[3,4b]-indole, 6-chloro-7-methyl-8-fluoro-1,2,3,4-tetrahydro-9H-pyrido[3,4b]-indole, 5-dimethylamino-8-hydroxy-1,2,3,4-tetrahydro-9H-pyrido[3,4b]-indole, 6-nitro-8-butyl-1,2,3,4-tetrahydro-9H-pyrido[3,4b]-indole, 7-cyclohexyl-8-hydroxy-1,2,3,4-tetrahydro-9H-pyrido[3,4b]-indole, 6-[3-methyl-cyclohexyl]-8-methyl-1,2,3,4-tetrahydro-9H-pyrido[3,4b]-indole, 6-benzyl-8-fluoro-1,2,3,4-tetrahydro-9H-pyrido[3,4b]-indole, 5-cyclohexylmethyl-8-chloro-1,2,3,4-tetrahydro-9H-pyrido[3,4b]-indole, 6-carboxyl-8-bromo-1,2,3,4-tetrahydro-9H-pyrido[3,4b]-indole, 6-ethoxy-8-isopropyl-1,2,3,4-tetrahydro-9H-pyrido[3,4b]-indole, 6,8-dichloro-1,2,3,4-tetrahydro-9H-pyrido[3,4b]-indole, 6,8-dimethyl-1,2,3,4-tetrahydro-9H-pyrido[3,4b]-indole, 7,8-difluoro-2(N)-methyl-1,2,3,4-tetrahydro-9H-pyrido[3,4b]-indole, 6,8-dibutyl-2(N)-cyclopropylmethyl-1,2,3,4-tetrahydro-9H-pyrido[3,4b]-indole, 6,8-dibromo-2(N)-cyclohexenylmethyl-1,2,3,4-tetrahydro-9H-pyrido[3,4b]-indole, 8-chloro-2(N)-benzyl-1,2,3,4-tetrahydro-9H-pyrido[3,4b]-indole, 8-fluoro-4-methyl-2(N)-cyclohexyl-1,2,3,4- tetrahydro-9H-pyrido[3,4b]-indole, 6-methylamine-8-chloro-3-isopropyl-1,2,3,4-tetrahydro-9H-pyrido[3,4b]-indole, and 6-chloromethyl-8-chloro-1,2,3,4-tetrahydro-9H-pyrido[3,4b]-indole.

The compounds of the present invention are known to form hydrates and solvates with appropriate solvents. Preferred solvents for the preparation of solvate forms include water, alcohols, tetrahydrofuran, DMF, and DMSO. Preferred alcohols are methanol and ethanol. Other appropriate solvents may be selected based on the size of the solvent molecule. Small solvent molecules are preferred to facilitate the corresponding solvate formation. The solvate or hydrate is typically formed in the course of recrystallization or in the course of salt formation. One useful reference concerning solvates is Sykes, Peter, *A Guidebook to Mechanism in Organic Chemistry*, 6, 56, (1986, John Wiley & Sons, New York). The term "solvate" as used herein includes hydrate forms such as monohydrate and dihydrates.

The compounds of the present invention can be prepared using chemical processes that are understood in the art; however, the most preferred method for preparing the formula (I) compounds of this invention utilizes the process of Scheme IV.

A compound of formula I, may be prepared by contacting glyoxylic acid with an amine of formula (h). This Pictet-Spengler type reaction is generally applicable, provides desirable yields, and produces stable intermediates. Further, the product of the reaction typically may be directly isolated as the desired salt.

Compound d in Scheme I is used as a starting material for compounds of Formula I. These compounds are commercially available or may be prepared using the well-known Fischer indole synthesis applied to tryptamines. The Fischer synthesis is represented by Scheme I.

Scheme I

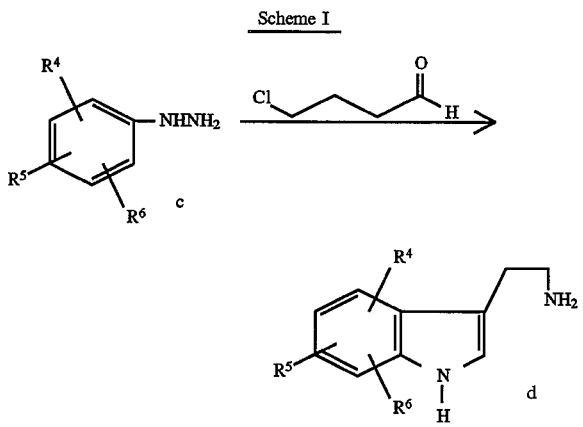

The chlorobutanal compound used in Scheme I may be prepared through the hydrogenation of chlorobutyryl chloride. The hydrogenation may be facilitated by the use of a catalyst such as Pd/C. Other halobutanal compounds may be suitable for the Scheme I. The starting compounds c in Scheme I may be purchased or prepared using known methods. March, J., *Advanced Organic Chemistry Reactions, Mechanisms, and Structure*, 3rd (John Wiley & Sons, New York, 1985) see especially page 1163.

The Fischer synthesis is commonly begun by adding a suitable saturated base like sodium carbonate to a stirred suspension of the hydrazine salt in an organic solvent like chloroform. The hydrazine hydrochloride salt is one especially preferred hydrazine salt. The desired hydrazine free base is extracted with the organic phase. The oil is placed in an alcohol and water solution and treated with an appropriate base like sodium acetate. The halobutanal is added and the tube purged with an inert gas like nitrogen. The resulting mixture is placed in an oil bath which has been heated to about 90° C.–110° C. The mixture should be heated for about 17 to 19 hours. The mixture is allowed to cool to ambient temperature and is concentrated under reduced pressure. The residue is partitioned between a suitable organic and basic aqueous phase, such as chloroform/methanol and aqueous sodium carbonate. The organic phase may be concentrated and the resulting compound d purified by standard methods such as flash chromatography. If chromatography is used, fractions containing product may be combined and concentrated. The oil is dissolved in an appropriate solvent, such as diethyl ether containing about 1% alcohol. A preferred alcohol is methanol. The mixture may be treated with dry acid gas, such as dry HCl gas to produce the corresponding acid addition salt of the desired compound d.

One method for preparing Formula I compounds uses the Pictet-Spengler reaction as represented by Scheme II. The substituents are as defined hereinabove.

Scheme II

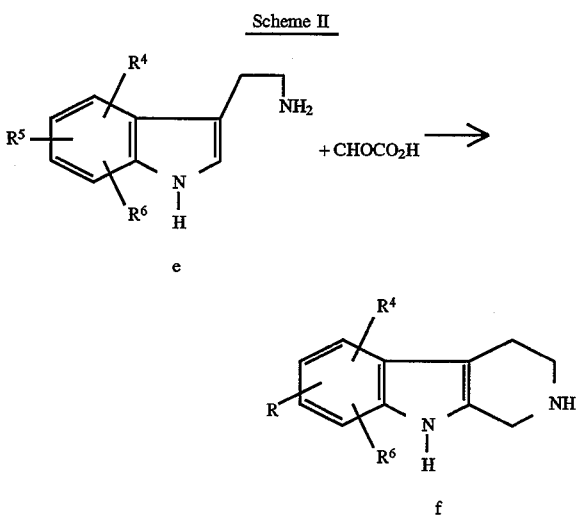

Generally, the Scheme II reaction is carried out by reacting compound e with the selected aldehyde in a suitable solvent such as ethanol or methanol for a period of about 1 to 50 hours. The precipitated reaction product is collected by common isolation methods, such as filtration, followed by decarboxylation with concentrated HCl and heating to afford a compound of formula f. The resulting material may be purified by recrystallization. If a compound with an $R^1$ substituent is desired, the reaction may be followed by a reductive alkylation. The reductive alkylation is represented by Scheme III.

Scheme III

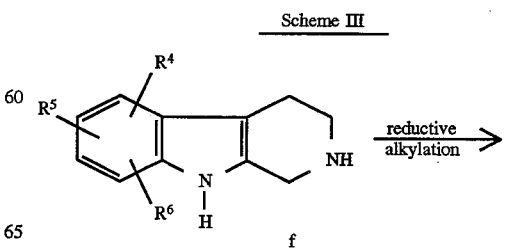

-continued
Scheme III

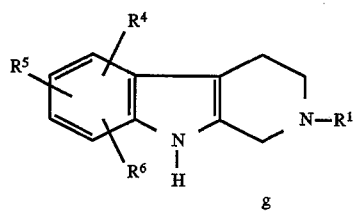

A protic acid and aldehyde solution is commonly added to an aqueous solution of compound f. The most preferred protic acid is formic acid. The most preferred aldehyde is formaldehyde. The artisan can readily choose other appropriate reagents to facilitate the reductive alkylation. The resulting solution is refluxed for a period of about 4 to 80 hours. After reflux the solution should be made basic using an appropriate base such as potassium carbonate. The desired product can then be extracted with an appropriate organic phase, such as chloroform. The product can be dried, concentrated, and purified by known methods such as flash chromatography.

Scheme IV

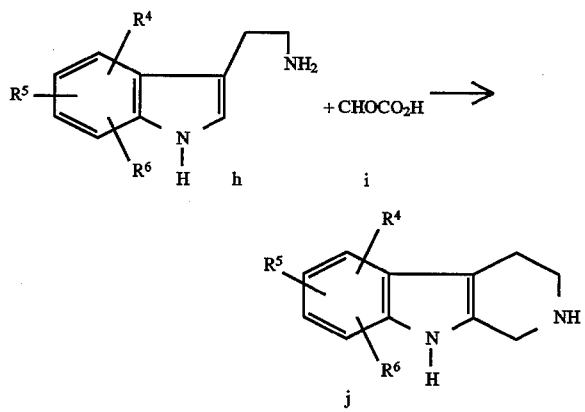

Compound h and compound i are contacted in a suitable aqueous solution. The reaction mixture may be neutralized with an appropriate base, such as potassium carbonate. Typically, the reaction mixture is stirred for from about 1 to about 48 hours; however, the reaction time may be adjusted if desirable. The resulting material is dissolved in a aqueous solvent and acidified by slow addition of a protic acid such as HCl. The mixture is heated and additional acid added. The resulting material can be isolated, and dissolved in an aqueous solvent. The resulting mixture is made basic followed by extraction with an organic phase, such as chloroform. The product can be isolated through solvent removal followed by chromatographic isolation, such as silica gel chromatography, or other common isolation techniques. Typically the product is isolated as the acid addition salt. Appropriate salt forms are discussed supra.

The following Examples further illustrate the preparation of certain of the Formula I compounds. The examples are illustrative only, and are not intended to limit the scope of the invention.

The column chromatography procedures used standard flash chromatography techniques. One well-known reference describing appropriate flash chromotagraphy techniques is Still, W. C. Kahn, and Mitra, J. Org. Chem., 43, 2932, (1978). Fractions containing product were generally evaporated under reduced vacuum to provide the product.

The hydrochloride salt of the particular compound was prepared by placing the free base into diethyl ether containing an alcohol such as methanol or other suitable solvent mixture. While stirring this ether solution, a solution of HCl in diethyl ether was added dropwise until the solution became acidic. Alternatively, the ether solution was treated with dry HCl gas.

The maleate salt of the particular compound was prepared by placing the free base in ethyl acetate or other suitable solvent and treating with maleic acid. The precipitate formed was filtered and dried to provide the corresponding hydrochloride or maleate salt of the free base.

Preparation 1

Preparation of 4-chlorobutanal

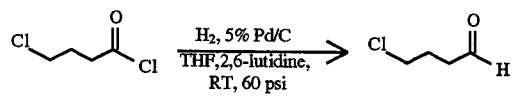

4-Chlorobutyryl chloride (300 g, 2.13 mol.) was dissolved in dry THF (3 L). To this solution was added 2,6-lutidine (252 mL) followed by 5% Pd/C (30 g). This mixture was placed in a Parr hydrogenator and shaken under 60 psi of hydrogen for 6 hours. The mixture was purged with nitrogen, filtered, washing the catalyst with THF (500 mL), and concentrated at room temperature under reduced pressure. Distillation afforded 4-chlorobutanal (148.3 g) as a colorless liquid.

Preparation 2

7-bromo-1H-indole-3-ethanamine

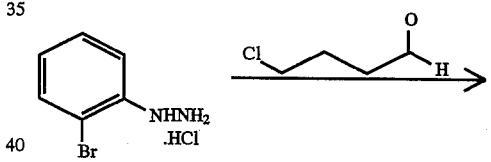

A 25.8 g sample of 2-bromophenylhydrazine hydrochloride was partitioned between 1 N NaOH and chloroform. The organic layer was separated and the aqueous portion was extracted with chloroform. The combined organic extracts were dried (Na$_2$SO$_4$) and concentrated to yield the free hydrazine as an oil.

The oil was stirred in 100 mL of methanol while 4-chlorobutyraldehyde (12.3 g) was added. The resulting solution was transferred to a sealable tube and purged with nitrogen. The tube was sealed and the reaction mixture was heated in an oil bath maintained at 95° C. for 14 hours. The resulting mixture was allowed to cool and concentrated to a residue which was partitioned between 1N NaOH and chloroform. The combined organic extracts were dried and concentrated to an oil. The oil was chromatographed on silica gel using a gradient of 0–10% methanol in chloroform. Fractions containing product were concentrated to an oil which was taken up in a small amount of methanol and added to ethereal HCl. A solid was collected, washed with diethyl ether and vacuum dried at 50° C.
Yield: 7.32 g
Yield: 23%
M.P.: 260°–262° C.
Elemental Analysis: C 43.55: H 4.41: N 10.03.

Preparation 3

7-methoxy-1H-indole-3-ethanamine

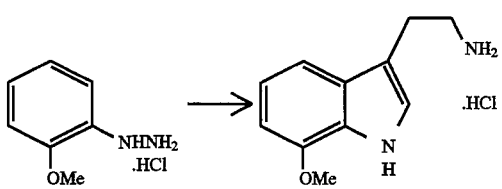

A 15.8 g sample of 2-methoxyphenylhydrazine hydrochloride and a 26.3 g sample of 4-phthalimidobutyraldehyde diethyl acetal were stirred in ethanol. The mixture was heated at reflux for 2 hours. The reaction mixture was allowed to cool and was concentrated to a residue.

The resulting residue was dissolved in 750 mL ethanol and 15.5 g hydrazine hydrate was added. The mixture was heated at reflux for 14 hours. A 70 mL sample of 5N HCl was added and the mixture was allowed to cool. The cooled mixture was concentrated to a residue. The residue was partitioned between 1N NaOH and chloroform. The organic portion was separated and the aqueous portion was extracted with chloroform. The combined organic extracts were dried (Na$_2$SO$_4$) and concentrated to an oil. The oil was chromatographed on silica gel using a gradient of 0–10% methanol in chloroform. Fractions containing product were concentrated to an oil which was taken up into a small amount of methanol and added to ethereal HCl. A solid was collected, washed with diethyl ether, and vacuum dried at 50° C. to afford a white solid.

EXAMPLE 1

7-methyl-8-bromo-1,2,3,4-tetrahydro-9H-pyrido[3,4b]-indole

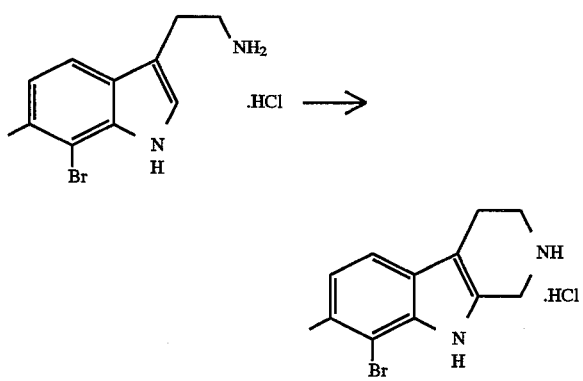

A 3.0 g sample of 6-methyl-7-bromo-1H-indole-3-ethanamine hydrochloride was dissolved in warm water. A solution of glyoxylic acid monohydrate (1.0 g) in water was added. The solution was adjusted to pH 4 using either potassium hydroxide or hydrochloric acid. A solid was suspended in water and concentrated HCl was added slowly. The mixture was boiled. A solid was collected, washed with water, and vacuum dried. The solid was partitioned between 1N NaOH and chloroform. The organic portion was dried and concentrated to a residue which was chromatographed on silica gel using methanol in chloroform. The desired fractions were pooled and concentrated to a solid which was dissolved in methanol, treated with gaseous HCl, and diluted with ether. A solid was collected, washed with ether, and dried.

Yield: 48%
Melting Point: 321° C.
Elemental Analysis: C 47.83; H 4.89; N 9.30.

EXAMPLE 2

8-methoxy-1,2,3,4-tetrahydro-9H-pyrido[3,4b]-indole

The desired product was prepared using substantially the process of Example 1, except that the starting material was 7-methoxy-1H-indole-ethanamine.

Melting Point: 207°–209° C.
Elemental Analysis: C 60.17; H 5.56; N 8.60.

EXAMPLE 3

8-methoxy-2(N)-propyl,2,3,4-tetrahydro-9H-pyrido[3,4b]-indole

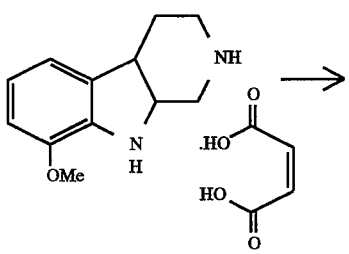

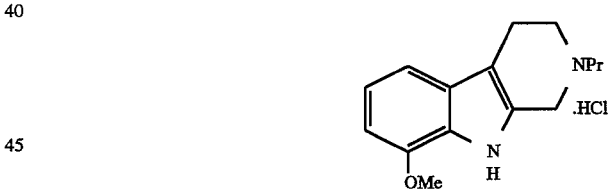

A sample of 8-methoxy-1,2,3,4-tetrahydro-9H-pyrido[3,4b]-indole was prepared substantially as described in Example 1. A 0.36 g sample of the indole was contacted with 1 g K$_2$CO$_3$ and the mixture was purged with nitrogen. A 40 mL sample of CH$_3$CN was added to the resulting mixture. A 0.12 mL sample of 1-iodopropane was added. The mixture was maintained under nitrogen and stirred in the dark. The resulting mixture was extracted. The organic phase was dried, evaporated, and chromatographed. The desired fractions were evaporated, taken up into methanol:ethyl acetate. The resulting mixture was added to a stirring ether solution through which gaseous HCl was bubbled. The resulting solid was vacuum dried, recrystallized, and evaporated to yield the desired product.

Yield: 0.10 g
Melting Point: 282°–284° C.
Elemental Analysis: C 64.45; H 7.67; N 9.91.

EXAMPLE 4

8-methoxy-2(N)-methyl-1,2,3,4-tetrahydro-9H-pyrido[3,4b]-indole

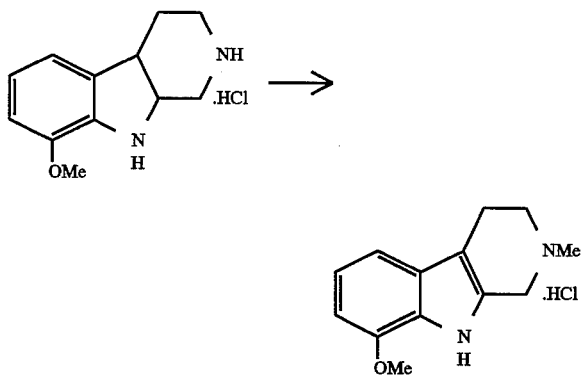

A sample of 8-methoxy-1,2,3,4-tetrahydro-9H-pyrido[3,4b]-indole was prepared substantially as described in Example 1. The indole (1 g), NaOAc (0.34 g), NaBH$_3$CN (0.53 g), methanol (50 mL), and HOAc (1.0 g) were stirred. A 1.36 g (37% in 10 mL methanol) sample of CH$_2$O was added to the indole mixture.

The reaction was quenched using an acid, then made basic, and extracted. The organic was dried, evaporated, and chromatographed. The desired fractions were evaporated and taken up into methanol/ethyl acetate. The resulting mixture was added to ethereal HCl. The resulting solid was collected and vacuum dried.

Yield: 0.84 g (79%)
Melting Point: 291°–294° C.
Elemental Analysis: C 62.06; H 6.97; N 11.32.

EXAMPLE 5

8-methoxy-2(N)-cyclopropylmethyl-1,2,3,4-tetrahydro-9H-pyrido[3,4b]-indole

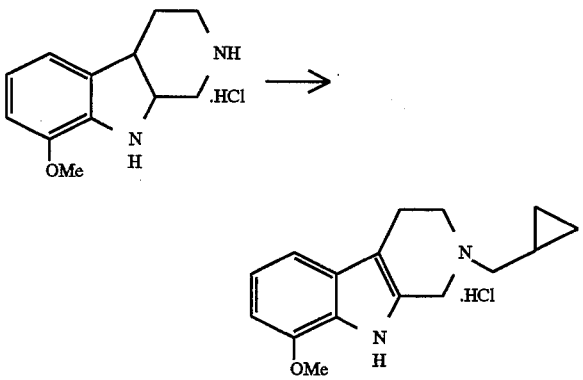

The desired product was prepared using appropriate reagents and the process substantially as described in Example 4.

Yield: 88%
Melting Point: 285°–287° C.
Elemental Analysis: C 65.76; H 7.47; N 9.47.

EXAMPLE 6

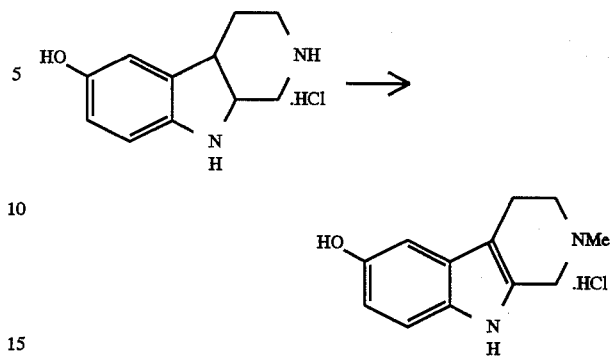

The desired product can be prepared using appropriate reagents and the process substantially as described in Example 4.

EXAMPLE 7

7,8-dimethyl-1,2,3,4-tetrahydro-9H-pyrido[3,4b]-indole

A 2.30 g sample of 6,7-dimethyl-1H-indole-ethanamine was dissolved in a mixture of water and isopropanol with heating. A 1.03 g sample of glyoxilic acid monohydrate in 10 mL of water was added to the flask. The solution was allowed to cool and made basic by the addition of potassium hydroxide. The reaction was stirred for 48 hours. The resulting solid was isolated by filtration and washed with water. The solid was dissolved in 50 mL of water and the solution was acidified by the slow addition of concentrated HCl. Heating was initiated and an additional 5 mL of concentrated HCl was added. The resulting solid was isolated by decanting and dissolved in 10 mL of water. This solution was made basic by the addition of potassium hydroxide and extracted using 1:3 isopropanol:CHCl$_3$. Separation and concentration of the organic layer gave a viscous oil which was purified via chromatography. The oil was dissolved in ethyl acetate and gaseous HCl was bubbled into the solution to form the hydrochloride salt. The solid hydrochloride salt was isolated by filtration and dried in a vacuum oven.

Yield: 54%
Melting Point: 330° C.
Elemental Analysis: C 65.75; H 7.29; N 11.62.

EXAMPLE 8

6-methyl-8-bromo-1,2,3,4-tetrahydro-9H-pyrido[3,4b]-indole

The desired 6-methyl-8-bromo-1,2,3,4-tetrahydro-9H-pyrido[3,4b]-indole was prepared using appropriate reagents and the process substantially as described in Example 7.

Yield: 57%
Melting Point: 346° C.
Elemental Analysis: C 48.04; H 4.68; N 9.30.

EXAMPLE 9

6,8-difluoro-1,2,3,4-tetrahydro-9H-pyrido[3,4b]-indole

The desired 6,8-difluoro-1,2,3,4-tetrahydro-9H-pyrido[3,4b]-indole was prepared using appropriate reagents and the process substantially as described in Example 7.

Yield: 5%
Melting Point: 350° C.
Elemental Analysis: C 53.90; H 4.49; N 11.23.

EXAMPLE 10

8-bromo-1,2,3,4-tetrahydro-9H-pyrido[3,4b]-indole

The desired 8-bromo-1,2,3,4-tetrahydro-9H-pyrido[3,4b]-indole was prepared using appropriate reagents and the process substantially as described in Example 7.
Yield: 4%
Melting Point: 337.8° C.
Elemental Analysis: C 46.17; H 4.26; N 9.52.

The following were prepared by the process substantially as described in Example 7.

8-fluoro-1,2,3,4-tetrahydro-9H-pyrido[3,4b]-indole
Yield: 48%
Melting Point: 329.5° C.
Elemental Analysis: C 58.58; H 5.43; N 12.37.
    6-chloro-1,2,3,4-tetrahydro-9H-pyrido[3,4b]-indole;
Yield: 63%
Melting Point: 317.9° C.
    6-bromo-1,2,3,4-tetrahydro-9H-pyrido[3,4b]-indole;
Yield: 19%
Melting Point: 310.9° C.
    6-fluoro-1,2,3,4-tetrahydro-9H-pyrido[3,4b]-indole;
Yield: 38%
Melting Point: 316.6° C.

EXAMPLE 11

7-methyl-8-chloro-1,2,3,4-tetrahydro-9H-pyrido[3,4b]-indole

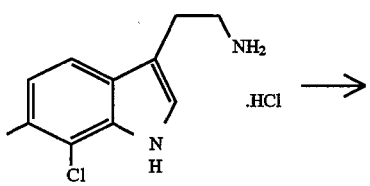

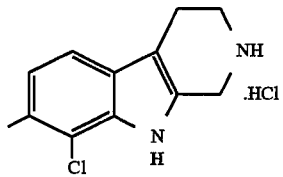

The desired product was prepared using the process substantially as described in Example 1 except that the starting material was 6-methyl-7-chloro-1H-indole-3-ethanamine hydrochloride.
Yield: 70%

The resulting material was boiled in ethanol. The resulting product was collected, washed with ethanol, and vacuum dried.
Yield: 58%
Melting Point: 330°–334° C.
Elemental Analysis: C 55.88; H 5.47; N 10.93.

The following were prepared using the process substantially as described above in Example 11.

7-methyl-8-chloro-1,2,3,4-tetrahydro-9H-pyrido[3,4b]-indole
Melting Point: 350°–352° C.
Elemental Analysis: C 55.65; H 5.68; N 10.39.
    8-chloro-1,2,3,4-tetrahydro-9H-pyrido[3,4b]-indole
Melting Point: 335°–337° C.
Elemental Analysis: C 53.93; H 4.88; N 11.09.
    7-bromo-8-methyl-1,2,3,4-tetrahydro-9H-pyrido[3,4b]-indole
Melting Point: 323°–325° C.

Elemental Analysis: C 47.85; H 4.84; N 9.08.

EXAMPLE 12

7-methyl-1,2,3,4-tetrahydro-9H-pyrido[3,4b]-indole

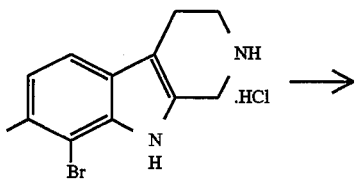

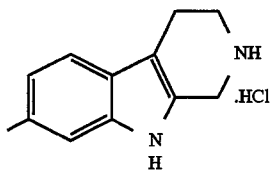

A sample of 7-methyl-8-bromo-1,2,3,4-tetrahydro-9H-pyrido[3,4b]-indole was reacted with hydrogen in the presence of Pd/C, ethanol, and triethylamine. The resulting material was filtered, concentrated and extracted. The organic phase was dried, concentrated, and vacuum dried. The resulting solid was taken up into methanol and added to ethereal HCl. A white solid was collected, washed with $Et_2O$, and vacuum dried.
Yield: 56%
Melting Point: 310°–312° C.
Elemental Analysis: C 64.79; H 6.89; N 12.47.

EXAMPLE 13

8-methyl-1,2,3,4-tetrahydro-9H-pyrido[3,4b]-indole

The desired product was prepared using the process substantially as described in Example 12.
Yield: 46%
Melting Point: 318°–320° C.
Elemental Analysis: C 64.53; H 6.94; N 12.43.

As noted above, the compounds of the present invention are useful in blocking the effect of serotonin or other agonists at $5-HT_2$ receptors. Thus, the present invention also provides a method for blocking $5-HT_2$ receptors in mammals comprising administering to a mammal requiring blocking of a $5-HT_2$ receptor a receptor blocking dose of a compound of the invention.

The term "receptor blocking dose", means an amount of compound necessary to block a $5-HT_2$ receptor in a mammal. The active compounds are effective over a wide dosage range. For example, dosages per day will normally fall within the range of about 0.05 to about 250 mg/kg of body weight. In the treatment of adult humans, the range of about 0.5 to 100 mg/kg, in single or divided doses, is preferred. The ranges of about 5 mg/kg to about 60 mg/kg and about 10 mg/kg to about 50 mg/kg are especially preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration, and therefore the above dosage ranges are not intended to limit the scope of the invention in any way. The compounds may be administered by a variety of routes such as oral, transdermal, subcutaneous, intranasal, intramuscular, and intravenous routes.

A variety of physiologic functions have been shown to be subject to be influenced by $5\text{-HT}_{2A}$, $5\text{-HT}_{2B}$, and/or $5\text{-HT}_{2C}$ receptors. Therefore, the compounds of the present invention can be used to treat a variety of disorders in mammals associated with these receptors. Such disorders include sleeping disorders, eating disorders, including bulimia and obesity, thermoregulation, sexual disorders, hyperactivity, excessive aggression, alcoholism, anxiety, obsessive-compulsive disorders, depression, psychosis, schizophrenia and schizophreniform disorders, panic disorders, Gilles de la Tourette syndrome, migraine headaches, and Alzheimer's Disease. Additionally, effects of the $5\text{-HT}_{2A}$, $5\text{-HT}_{2B}$, and/or $5\text{-HT}_{2C}$ receptors indicate that the compounds of the present invention can be useful for relieving the sensation of pain. Thus, the present invention also provides methods for treating the above disorders and for relieving the sensation of pain.

Several examples of more specific disorders which may be treated using compounds of this invention include, but are not limited to: (numerals in parenthesis refer to the DSM-III-R Classification Codes) Attention-deficit hyperactivity disorder (314.01), conduct disorders (312.20, 312.00, 312.90), primary degenerative dementia of the Alzheimer type, senile onset (290.30, 290.20, 290.21, 290.00), primary degenerative dementia of the Alzheimer type, presenile onset (290.11, 290.12, 290.13, 290.10), alcohol withdrawal delirium (291.00), alcohol hallucinosis (291.30), alcohol, dementia associated with alcoholism (291.20), cannabis, delusional disorder (292.11), cocaine, intoxication (305.60), hallucinogen, mood disorder (292.84), nicotine withdrawal (292.00), phencyclidine or similarly acting arylcyclohexylamine intoxication (305.90), other psychoactive substance intoxication (305.90), delirium (293.00), dementia (294.10), organic delusional disorder (293.81), organic hallucinosis (293.82), organic mood disorder (293.83), organic anxiety disorder (294.80), organic personality disorder (310.10), organic mental disorder (294.80), schizophrenia, catatonic (295.21, 295.22, 295.23, 295.24, 295.25, 295.20), schizophrenia, disorganized (295.11, 295.12, 295.13, 295.14, 295.15, 295.00), schizophrenia, paranoid (295.31, 295.32, 295.33, 295.34, 295.35, 295.00), schizophrenia, undifferentiated (295.91, 295.92, 295.93, 295.94, 295.95, 295.00), schizophrenia, residual (295.61, 295.62, 295.63, 295.64, 295.65, 295.60), delusional (paranoid disorder (297.10), schizophreniform disorder (295.40), schizoaffective disorder (295.70), induced psychotic disorder (297.30), bipolar disorder, mixed (296.61, 296.62, 296.63, 296.64, 296.65, 296.66, 296.60), bipolar disorder, manic (296.41, 296.42, 296.43, 296.44, 296.45, 296.46, 296.40), bipolar disorder, depressed (296.51, 296.52, 296.53, 296.54, 296.55, 296.56, 296.50), major depression, single episode (296.21, 296.22, 296.23, 296.24, 296.25, 296.26, 296.20), major depression, recurrent (296.31, 296.32, 296.33, 296.34, 296.35, 296.36, 296.30), obsessive compulsive disorder (300.30), post-traumatic stress disorder (309.89), generalized anxiety disorder (300.02), hypochondriasis (300.07), somatization disorder (300.81), male erectile disorder (302.72), intermittent explosive disorder (312.34), impulse control disorder (312.39), paranoid (301.00), schizoid (301.20), schizotypal (301.22), antisocial (301.70), and borderline (301.83). *Diagnostic and Statistical Manual of Mental Disorders*, 3rd Ed. Revised, (1980), prepared by the Task Force on Nomenclature and Statistics of the American Psychiatric Association.

One particularly useful embodiment of this invention is that it provides selective ligands for the $5\text{-HT}_{2B}$ receptor. Now $5\text{-HT}_{2B}$ receptors can be selectively modulated using compounds of this invention at rates set forth above for blocking the effects of agonists at $5\text{-HT}_{2B}$ receptors. The selective affinity may provide treatments with fewer side effects and will facilitate the development of additional therapeutic agents.

Certain compounds of the present invention have been found to display excellent activity in a $5\text{-HT}_{2B}$ receptor binding assay which measures the affinity of the compounds to bind to $5\text{-HT}_{2B}$ receptors. Further, certain of the compounds bind to the $5\text{-HT}_{2C}$ receptor and/or $5\text{-HT}_{2A}$ receptor. The assays were conducted by the following procedures.

$5\text{-HT}_{2A}$ and $5\text{-HT}_{2C}$ Assay

I. Biological Reagent Preparation.

Beef brain was removed immediately after slaughter, and choroid plexus were dissected over ice. Male Sprague-Dawley rats weighing 125–150 g (Harlan Industries, Cumberland, Ind.) were killed by decapitation. The brain of each was immediately removed and the cerebral cortex was dissected over ice. Tissues were homogenized in 9 volumes of 0.32 mol/L sucrose and centrifuged at 1,000 ×g for 10 minutes. The supernatant was centrifuged at 17,000 ×g for 20 minutes. The pellet was suspended in 100 volumes of 50 mM Tris-HCl (pH7.4), incubated at 37° C. for 10 minutes and centrifuged at 50,000 ×g for 10 minutes, and the process was repeated three times. The final pellets were frozen at −70° C. and used within 2 weeks. Pellets were rehydrated with physiological buffer prior to use.

II. Assay Procedure.

Radioligand binding assays for $5\text{-HT}_{2C}$ and $5\text{-HT}_{2A}$ receptors were conducted according to described methods. The assays can be conducted as described by Hoyer D, Functional correlates of serotonin $5\text{-HT}_1$ recognition sites, *J. Receptor Res.*, 8, 59–81 (1988) and Hoyer D, Engel G, Kalkman HO Molecular pharmacology of $5\text{-HT}_1$ and $5\text{-HT}_2$ recognition sites in rat and pig brain membranes: Radioligand binding studies with [$^3$H]5-HT, [$^3$H]8-OH-DPAT, (−) [$^{125}$I]iodocyanopindolol, [$^3$H]mesulergine and [$^3$H] ketanserin, *Eur. J. Pharmacol.*, 118, 13–23 (1985).

For $5\text{-HT}_{2C}$ receptor assays increasing concentrations of experimental compound, 50 mM Tris HCl buffer pH 7.4, and tritiated mesulergine (2.0 nM) ($^3$H ligand) were combined in polystyrene tubes at room temperature. The reaction was initiated by the addition of the resuspended choroid plexus tissue which had been preincubated at 37° C. for 20 minutes. The reaction mixture was incubated in a 37° C. water bath for 15 minutes.

For $5\text{-HT}_{2A}$ receptor assays increasing concentrations of experimental compound, 50 mM Tris HCl buffer pH 7.4, and tritiated ketanserin (1 nM) ($^3$H ligand) were combined in polystyrene tubes at room temperature. The reaction was initiated by the addition of the resuspended rat cerebral cortex tissue which had been preincubated at 37° C. for 20 minutes. The reaction mixture was incubated in a 37° C. water bath for 30 minutes.

The above assays were modified after a number of compounds had been screened to accommodate the unexpectedly high potency of the compounds of this invention in the $5\text{-HT}_{2C}$ assay. The concentration range of the experimental compound in the assays was changed from [0.1 to 1000 (nM)] to [0.1 to 100 (nM)] to optimize the use of reagents and analysis time.

The reactions were terminated by rapid filtration, (Brandel Cell Harvestor), through Whatman GF/B glass filters that had been presoaked in Tris buffer pH 7.4. The filters were then washed 2 times with 5 ml of ice cold Tris buffer pH 7.4. Washed filters were placed in scintillation vials and 10 ml RedySolv, (Brandel), was added and samples were counted in a Searle D-300 beta counter. Means and standard error statistics were calculated for triplicate experimental determinations in certain cases. Mean values were obtained from three or more separate determinations. The incubation time for the reaction mixture was 15 minutes at 37° C.

Concentrations that caused a 50% inhibition of radioligand binding (IC$_{50}$) and Hill coefficient were obtained by computer-assisted regression analysis.

Compounds of this invention were tested and demonstrated activity at the 5-HT$_{2A}$ and/or 5-HT$_{2C}$ receptors.

Another test which is useful for screening the compounds of this invention can be completed as follows:

Radioligand Binding Studies

Membrane preparation from transformed cells. Suspension cells expressing the cloned rat 5-HT$_{2B}$ receptor were harvested by centrifugation at 2,200 ×g for 15 min at 4° C. Kursar, J. D., D. L. Nelson, D. B. Wainscott, M. L. Cohen, and M. Baez, Mol. Pharmacol., 42: 549–557 (1992). Membranes for the binding assays were prepared by vortexing the pellet in 50 mM Tris-HCl, pH 7.4 (0.5×10$^9$ cells/30 ml). The tissue suspension was then centrifuged at 39,800 ×g for 10 min at 4° C. This procedure was repeated for a total of three washes, with a 10 minute incubation at 37° C. between the first and second wash. The final pellet was homogenized in 67 mM Tris-HCl, pH 7.4 (at 20–40 and 12.5 million cells/ml, original cell number, for cells expressing low and relatively high levels of the 5-HT$_{2B}$ receptor, respectively) using a Tissumizer (Tekmar, Cincinnati, Ohio), setting 65 for 15 seconds.

[$^3$H]5-HT binding studies. Binding assays were automated using a Biomek 1000 (Beckman instruments, Fullerton, Calif.) and were performed in triplicate in 0.8 ml total volume. Membrane suspension, 200 μl, (0.04–0.27 mg protein) and 200 μl of drug dilution in water were added to 400 μl of 67 mM Tris-HCl, pH 7.4, containing [$^3$H]5-HT, pargyline, CaCl$_2$, and L-ascorbic acid. Final concentrations of pargyline, CaCl$_2$ and L-ascorbic acid were 10 μM, 3 mM and 0.1%, respectively. Tubes were incubated at 37° C. for 15 min or at 0° C. for 2 hours (binding equilibria were verified for both of these conditions), then rapidly filtered using a Brandel cell harvester (Model MB-48R; Brandel, Gaithersburg, Md.) through Whatman GF/B filters which had been presoaked in 0.5% polyethylenimine and pre-cooled with ice-cold 50 mM Tris-HCl, pH 7.4. The filters were then washed rapidly four times with one ml ice-cold 50 mM Tris-HCl, pH 7.4. The amount of [$^3$H]5-HT trapped on the filters was determined by liquid scintillation spectrometry (Ready Protein and Beckman automated using a Biomek 1000 (Beckman Instruments, Fullerton, Calif.) and were performed in triplicate in 0.8 ml total volume. Membrane suspension, 200 μl, (0.04–0.27 mg protein) and 200 μl of drug dilution in water were added to 400 μl of 67 mM Tris-HCl, pH 7.4, containing [$^3$H]5-HT, pargyline, CaCl$_2$, and L-ascorbic acid. Final concentrations of pargyline, CaCl$_2$ and L-ascorbic acid were 10 μM, 3 mM and 0.1%, respectively. Tubes were incubated at 37° C. for 15 min or at 0° C. for 2 hours (binding equilibria were verified for both of these conditions), then rapidly filtered using a Brandel cell harvester (Model MB-48R; Brandel, Gaithersburg, Md.) through Whatman GF/B filters which had been presoaked in 0.5% polyethylenimine and precooled with ice-cold 50 mM Tris-HCl, pH 7.4. The filters were then washed rapidly four times with one ml ice-cold 50 mM Tris-HCl, pH 7.4. The amount of [$^3$H]5-HT trapped on the filters was determined by liquid scintillation spectrometry (Ready Protein and Beckman determined for best fit to a one-site or a two-site binding model using a partial E-test. De Lean, A., A. A. Hancock, and R. J. Lefkowitz, Mol. Pharmacol., 21:5–16 (1981). The following equation was used for a one-site binding model, $$\text{Bound} = \frac{B_{max} \times [L]}{K_d + [L]}$$

where Bound=amount of [$^3$H]5-HT specifically bound, $B_{max}$=maximum number of binding sites, $K_d$=equilibrium dissociation constant and [L]=free concentration of [$^3$H]5-HT, or a two-site binding model, $$\text{Bound} = \frac{B_{max1} \times [L]}{K_{d1} + [L]} + \frac{B_{max2} \times [L]}{K_{d2} + [L]}$$

where Bound=amount of [$^3$H]5-HT specifically bound, $B_{max1}$=maximum number of high affinity binding sites, $B_{max2}$=maximum number of low affinity binding sites, $K_{d1}$=equilibrium dissociation constant for the high affinity site, $K_{d2}$=equilibrium dissociation constant for the low affinity site and [L]=free concentration of [$^3$H]5-HT. The IC$_{50}$ values from the competition assays, the binding parameters for the IP$_3$ standard curve and the EC$_{50}$ and E$_{max}$ values from the IP$_3$ assays were determined by nonlinear regression analysis of four parameter logistic equations (Systat, Systat Inc., Evanston, Ill.). De Lean, A., A. A. Hancock, and R. J. Lefkowitz, Mol. Pharmacol., 21:5–16 (1981). The IC$_{50}$ values were converted to K$_i$ values using the Cheng-Prusoff equation. Cheng, Y., and W. H. Prusoff, Biochem. Pharmacoi., 22:3099–3108 (1973).

Compounds of this invention were tested using the described in vitro assay. Results of the radioligand binding experiments are illustrated in Table I. The values reported in Table I are expressed as K$_i$ calculated as described infra.

TABLE I

| Example # | Rat 2B | Human 2B | Rat 2A | Human 2A | Rat 2C | Human 2C |
|---|---|---|---|---|---|---|
| 1 | 3.17 | — | 15.74 | 21.74 | 14.17 | 18.19 |
| 2 | 34.49 | — | — | — | — | — |
| 3 | 114.16 | — | — | — | — | — |
| 4 | 71.75 | — | — | — | — | — |
| 5 | 97.53 | — | — | — | — | — |
| 6 | 4609.36 | — | — | — | — | — |
| 7 | 15.83 | — | — | — | — | — |
| 8 | 13.98 | 16.43 | 47.00 | 41.71 | 34.86 | 38.61 |
| 9 | 57.89 | — | — | — | — | — |
| 10 | 6.20 | 9.68 | 25.61 | 22.72 | 22.41 | 13.22 |

Another useful assay for determining 5-HT2B receptor binding in vitro is the following method:

Male Wistar rats (150–375 g; Laboratory Supply, Indianapolis, Ind.) were sacrificed by cervical dislocation, and longitudinal section of the stomach fundus were prepared for in vitro examination. Four preparations were obtained from one rat fundus. Ring preparations of the extracted jugular vein were prepared as described by Hooker; Blood Vessels, 14:1 (1977) and Cohen, M. L. J. Pharamcol. Exp. Ther., 227:327 (1983). Tissues were mounted in organ baths containing 10 mL of modified Krebs solution of the following composition (millimolar concentrations): NaCl, 118.2; KCl, 4.6; CaCl$_2$·H$_2$O, 1.6; KH$_2$PO$_4$, 1.2; MgSO$_4$, 1.2; dextrose, 10.0; and NaHCO$_3$, 24.8. Tissue bath solutions were maintained at 37° C. and equilibrated with 95% O$_2$ and 5% CO$_2$. Tissues were placed under optimum resting force (4 g) and were allowed to equilibrate for approximately 1 hour before exposure to the test compound. Isometric contractions were recorded as changes in grams of force on a Beckman Dynograph with Statham UC-3 transducers.

Determination of Apparent Antagonist Dissociation Constant:

Noncumulative contractile concentration-response curves for serotonin in the fundus and cumulative concentration response curves in the jugular vein were obtained by a stepwise increase in concentration after washing out the preceding concentrations every 15-20 minutes. Each agonist concentration remained in contact with the tissue for approximately 2 minutes and maximum response to each compound concentration was measured. $ED_{50}$ values were taken as the concentration of agonist that produced half-maximal contraction. After control responses were obtained, tissues were incubated with an appropriate concentration of buffer or antagonist for 1 hour. Responses to serotonin were then repeated in the presence of an antagonist. Concentration responses utilized only one agonist and one antagonist concentration per tissue. In general, successive agonist responses in the presence of buffer treatment were unaltered (average dose ratio was 1.28+/−0.21).

Apparent antagonist dissociation constants ($K_B$) were determined for each concentration of antagonist according to the following equation:

$$K_B = [B]/(dose\ ratio - 1)$$

where [B] is the concentration of the antagonist and dose ratio is the $ED_{50}$ of the agonist in the presence of the antagonist divided by the control $ED_{50}$. Generally, parallel shifts in the concentration-response curves occurred in the presence of antagonists. The results were expressed as the negative logarithm of the $K_B$ (i.e., $-\log K_B$). Calculations were completed using known methods. Zaborowsky, B. R. *J. Pharmacol. Methods*, 4:4165 (1980).

Compounds of this invention were tested using the in vitro method (supra.) and demonstrated activity at the $5\text{-HT}_{2B}$ receptor.

Compounds exhibiting activity at the $5HT_{2B}$ receptor are useful for treating disorders related to the modulation of the $5HT_{2B}$ receptor. For example, compounds having $5HT_{2B}$ antagonist activity reduce the spasticity of the colon. These compounds are useful for the treatment of functional bowel disorders including irritable bowel syndrome and irritable bowel syndrome-related symptoms. The antispasmodic effect of such compounds can reduce abdominal pain associated with functional bowel disorders.

Compounds demonstrating activity at the $5HT_{2A}$ receptor are especially useful in the treatment or prevention of conditions related to modulation of the $5HT_{2A}$ receptor. Examples of such conditions include hypertension, sleep disorders, hallucinogenic activity, psychosis, anxiety, depression, thermoregulation, feeding disorders, and hypotension. Leonard, B. E., *International Clinical Psychopharmacology*, 7, 13–21 (1992).

The skilled artisan will recognize that psychosis or psychotic conditions are characterized by hallucinations, delusions, or grossly disorganized behavior which indicate that the patient suffers from gross impairment in reality testing. Therefore, drugs having antipsychotic activity can be useful for treating a variety of important psychotic conditions.

While it is possible to administer a compound of the invention directly without any formulation, the compounds are preferably employed in the form of a pharmaceutical formulation comprising a pharmaceutically acceptable excipient and at least one compound of the invention. Such compositions contain from about 0.1 percent by weight to about 90.0 percent by weight of a present compound. As such, the present invention also provides pharmaceutical formulations comprising a compound of the invention and a pharmaceutically acceptable excipient therefor.

In making the compositions of the present invention, the active ingredient is usually mixed with an excipient which can be a carrier, or a diluent or be diluted by a carrier, or enclosed within a carrier which can be in the form of a capsule, sachet, paper or other container. When the carrier serves as a diluent, it can be a solid, semi-solid, or liquid material which acts as a vehicle, excipient, or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

The compounds of the invention may be delivered transdermally, if desired. Transdermal permeation enhancers and delivery systems, including patches and the like, are well known to the skilled artisan.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxy- benzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For oral administration, a compound of this invention ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical carrier.

In order to more fully illustrate the operation of this invention, the following formulation examples are provided. The examples are illustrative only, and are not intended to limit the scope of the invention. The formulations may employ as active compounds any of the compounds of the present invention.

Formulation 1

Hard gelatin capsules are prepared using the following ingredients:

|  | Amount Per Capsule | Concentration by Weight (percent) |
|---|---|---|
| (+/−) 6-ethyl-8-chloro-1,2,3,4-tetrahydro-9H-pyrido[3,4-b]indole hydrochloride | 250 mg | 55.0 |
| starch dried | 200 mg | 43.0 |
| magnesium stearate | 10 mg | 2.0 |
|  | 460 mg | 100.0 |

The above ingredients are mixed and filled into hard gelatin capsules in 460 mg quantities.

Formulation 2

Capsules each containing 20 mg of medicament are made as follows:

|  | Amount Per Capsule | Concentration by Weight (percent) |
|---|---|---|
| 6-methyl-8-ethyl-1,2,3,4-tetrahydro-9H-pyrido[3,4b]indole (Z)-2-butenedioate | 20 mg | 10.0 |
| starch | 89 mg | 44.5 |
| microcrystalline cellulose | 89 mg | 44.5 |
| magnesium stearate | 2 mg | 1.0 |
|  | 200 mg | 100.0 |

The active ingredient, cellulose, starch, and magnesium stearate are blended, passed through a No. 45 mesh U.S. sieve and filled into a hard gelatin capsule.

Formulation 3

Capsules each containing 100 mg of medicament are made as follows:

|  | Amount Per Capsule | Concentration by Weight (percent) |
|---|---|---|
| 5-methyl-8-chloro-1,2,3,4-tetrahydro-9H-pyrido[3,4-b]indole (Z)-2-butenedioate | 100 mg | 30.00 |
| polyoxyethylene sorbitan monooleate | 50 mg | 0.02 |
| starch powder | 250 mg | 69.98 |
|  | 400 mg | 100.00 |

The above ingredients are thoroughly mixed and placed in an empty gelatin capsule.

Formulation 4

Tablets containing 10 mg of active ingredient are made as follows:

|  | Amount Per Tablet | Concentration by Weight (percent) |
|---|---|---|
| 7-methyl-8-phenoxy-1,2,3,4-tetrahydro-9H-pyrido[3,4-b]indole (Z)-2-butenedioate | 10 mg | 10.0 |
| starch | 45 mg | 45.0 |
| microcrystalline cellulose | 35 mg | 35.0 |
| polyvinylpyrrolidone (as 10% solution in water) | 4 mg | 4.0 |
| sodium carboxymethyl starch | 4.5 mg | 4.5 |
| magnesium stearate | 0.5 mg | 0.5 |
| talc | 1 mg | 1.0 |
|  | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

Formulation 5

A tablet formulation may be prepared using the ingredients below:

|  | Amount Per Tablet | Concentration by Weight (percent) |
|---|---|---|
| 6,8-difluoro-1,2,3,4-tetrahydro-9H-pyrido[3,4-b]indole (Z)-2-butanedioate | 250 mg | 38.0 |
| microcrystalline cellulose | 400 mg | 60.0 |
| silicon dioxide fumed | 10 mg | 1.5 |
| stearic acid | 5 mg | 0.5 |
|  | 665 mg | 100.0 |

The components are blended and compressed to form tablets each weighing 665 mg.

Formulation 6

Suspensions each containing 5 mg of medicament per 5 ml dose are as follows:

|  | per 5 ml of suspension |
|---|---|
| 5-chloro-8-bromo-1,2,3,4-tetrahydro-9H-pyrido[3,4-b]indole (Z)-2-butenedioate | 5 mg |
| sodium carboxymethyl cellulose | 50 mg |
| syrup | 1.25 ml |
| benzoic acid solution | 0.10 ml |
| flavor | q.v. |
| color | q.v. |
| water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| | Concentration by Weight (percent) |
|---|---|
| 7-chloro-8-methyl-1,2,3,4-tetrahydro-9H-pyrido[3,4b]-indole hydrochloride | 0.25 |
| ethanol | 29.75 |
| Propellant 22 | 70.00 |
| (chlorodifluoromethane) | |
| | 100.00 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

We claim:

1. A compound of Formula I

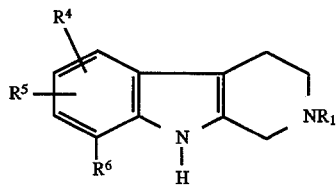

wherein:

$R^1$ is hydrogen, $C_1$–$C_3$ alkyl, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, or $C_7$–$C_{16}$ arylalkyl;

$R^4$ and $R^5$ are independently hydrogen, $C_1$–$C_3$ alkyl, $C_2$–$C_6$ alkenyl, halo, halo($C_1$–$C_6$)alkyl, halo ($C_2$–$C_6$) alkenyl, $COR^7$, $C_1$–$C_{10}$ alkanoyl, $CO_2R^{7'}$, ($C_1$–$C_6$ alkyl)$_m$ amino, $NO_2$, —$SR^7$, $OR^7$, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$) alkyl, or $C_7$–$C_{16}$ arylalkyl;

m is 1 or 2;

$R^7$ is hydrogen or $C_1$–$C_4$ alkyl;

$R^{7'}$ is $C_1$–$C_4$ alkyl;

$R^6$ is selected from the group consisting of $C_1$–$C_4$ alkyl, $OR^{5'}$, fluoro, bromo, iodo, and chloro;

$R^{5'}$ is selected from the group consisting of hydrogen and $C_1$–$C_4$ alkyl;

with the proviso that, when $R^1$ is hydrogen, $C_1$–$C_3$ alkyl, $C_3$–$C_8$ cycloalkyl-($C_1$–$C_3$) alkyl or $C_7$–$C_{16}$ arylalkyl;

$R^4$ is hydrogen or $C_1$–$C_3$ alkyl; and $R^5$ is hydrogen, $C_1$–$C_3$ alkyl, halo, or $OR^7$;

then $R^6$ must be selected from the group consisting of $OR^{5'}$, fluoro, bromo, iodo, and chloro; or a pharmaceutically acceptable salt or solvate thereof.

2. A compound of claim 1 with the additional proviso that, when $R_1$ is hydrogen or $C_1$–$C_3$ alkyl, then at least one of $R^4$ and $R^5$ is selected from $C_2$–$C_6$ alkenyl, halo($C_1$–$C_6$)alkyl, halo($C_2$–$C_6$)alkenyl, $COR^7$, $C_1$–$C_{10}$ alkanoyl, $CO_2R^{7'}$, ($C_1$–$C_6$ alkyl)$_m$amino, $NO_2$, -$SR^7$, substituted $C_3$–$C_8$ cycloalkyl, $C_3$–$C_8$ cycloalkyl, $C_3$–$C_8$ cycloalkyl-($C_1$–$C_3$) alkyl, $C_5$–$C_8$ cycloalkenyl-($C_1$–$C_3$)alkyl, and $C_7$–$C_{16}$ arylalkyl.

3. A compound of claim 2 wherein $R^4$ is selected from the group consisting of $C_1$–$C_{10}$ alkanoyl, $CO_2R^{7'}$, ($C_1$–$C_6$ alkyl)$_m$ amino, $NO_2$, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, and $C_7$–$C_{16}$ arylalkyl.

4. A compound of claim 3 wherein $R^4$ is selected from the group consisting of substituted $C_3$–$C_8$ cycloalkyl, $C_3$–$C_8$ cycloalkyl, and $C_3$–$C_8$ cycloalkyl-($C_1$–$C_3$)alkyl.

5. A compound of claim 1 with the additional proviso that, when $R_1$ is ($C_3$–$C_8$)cycloalkyl-($C_1$–$C_3$)alkyl, and one of $R^4$, $R^5$, and $R^6$ is selected from halo, $OR^{7'}$, $OR^{5'}$, and hydrogen; then (a) the other $R^4$, $R^5$, and $R^6$ groups must be selected from $OR^{7'}$, $OR^{5'}$, fluoro, bromo, iodo, and chloro; or (b) at least one of $R^4$ and $R^5$ must be selected from $C_2$–$C_6$ alkenyl, halo($C_1$–$C_6$)alkyl, halo($C_2$–$C_6$)alkenyl, $COR^7$, $C_1$–$C_{10}$ alkanoyl, $CO_2R^{7'}$, ($C_1$–$C_6$ alkyl)$_m$ amino, $NO_2$, —$SR^7$, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, and $C_7$–$C_{16}$ arylalkyl.

6. A compound of claim 5 wherein at least one of the group consisting of $R^4$ and $R^5$ is selected from $C_2$–$C_6$ alkenyl, halo($C_1$–$C_6$)alkyl, halo($C_2$–$C_6$)alkenyl, $COR^7$, $C_1$–$C_{10}$ alkanoyl, $CO_2R^{7'}$, ($C_1$–$C_6$ alkyl)$_m$ amino, $NO_2$, —$SR^7$, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, and $C_7$–$C_{16}$ arylalkyl.

7. A compound of claim 2 wherein $R^1$ is hydrogen.

8. A compound of claim 7 wherein $R^6$ is selected from the group consisting of fluoro, bromo, chloro, and $OR^{5'}$.

9. A compound of claim 8 wherein $R^{5'}$ is $C_1$–$C_2$ alkyl.

10. A compound of claim 9 wherein $R^4$ is hydrogen, $C_1$–$C_3$ alkyl, $C_2$–$C_6$ alkenyl, halo, halo($C_1$–$C_6$)alkyl, halo ($C_2$–$C_6$)alkenyl, $COR^7$, $C_1$–$C_{10}$ alkanoyl, $CO_2R^{7'}$, ($C_1$–$C_6$ alkyl)$_m$ amino, $NO_2$, —$SR^7$, or $OR^7$.

11. A compound of claim 2 wherein $R^5$ is at the 6-position.

12. A compound of claim 1 wherein $R^1$ is selected from the group consisting of substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, or $C_7$–$C_{16}$ arylalkyl.

13. A compound of claim 1 selected from the group consisting of 7-methyl-8-bromo-1,2,3,4-tetrahydro-9H-pyrido[3,4b]-indole, 8-methoxy-1,2,3,4-tetrahydro-9H-pyrido[3,4b]-indole, 7,8-dimethyl-1,2,3,4-tetrahydro-9H-pyrido[3,4b]-indole, 6-methyl-8-bromo-1,2,3,4-tetrahydro-9H-pyrido[3,4b]-indole, 6,8-difluoro-1,2,3,4-tetrahydro-9H-pyrido[3,4b]-indole, 8-bromo-1,2,3,4-tetrahydro-9H-pyrido[3,4b]-indole, 7-methyl-8-chloro-1,2,3,4-tetrahydro-9H-pyrido[$^{3,4}$b]-indole, 8-fluoro-1,2,3,4-tetrahydro-9H-pyrido[3,4b]-indole, 7-methyl-8-chloro-1,2,3,4-tetrahydro-9H-pyrido[3,4b]-indole, 8-chloro-1,2,3,4-tetrahydro-9H-pyrido[3,4b]-indole, 7-bromo-8-methyl-1,2,3,4-tetrahydro-9H-pyrido[3,4b]-indole, and 8-methyl-1,2,3,4-tetrahydro-9H-Pyrido[3,4b]-indole.

14. A pharmaceutical formulation comprising a compound of claim 1 and one or more pharmaceutically acceptable excipients.

15. A method for binding a 5-$HT_{2A}$ receptor in a mammal, comprising administering to the mammal a receptor-binding dose of a compound of Formula I

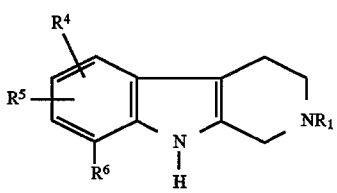

wherein:
- $R^1$ is hydrogen, $C_1$-$C_3$ alkyl, substituted $C_3$-$C_8$ cycloalkyl, $C_3$-$C_8$ cycloalkyl, $C_3$-$C_8$ cycloalkyl-($C_1$-$C_3$)alkyl, $C_5$-$C_8$ cycloalkenyl-($C_1$-$C_3$)alkyl, or $C_7$-$C_{16}$ arylalkyl;
- $R^4$ and $R^5$ are independently hydrogen, $C_1$-$C_3$ alkyl, $C_2$-$C_6$ alkenyl, halo, halo($C_1$-$C_6$)alkyl, halo($C_2$-$C_6$) alkenyl, $COR^7$, $C_1$-$C_{10}$ alkanoyl, $CO_2R^{7'}$, ($C_1$-$C_6$ alkyl)$_m$ amino, $NO_2$, —$SR^7$, $OR^7$, substituted $C_3$-$C_8$ cycloalkyl, $C_3$-$C_8$ cycloalkyl, $C_3$-$C_8$ cycloalkyl-($C_1$-$C_3$)alkyl, $C_5$-$C_8$ cycloalkenyl-($C_1$-$C_3$)alkyl, or $C_7$-$C_{16}$ arylalkyl;
- m is 1 or 2;
- $R^7$ is hydrogen or $C_1$-$C_4$ alkyl;
- $R^{7'}$ is $C_1$-$C_4$ alkyl;
- $R^6$ is selected from the group consisting of $C_1$-$C_4$ alkyl, $OR^{5'}$, fluoro, bromo, iodo, and chloro; and
- $R^{5'}$ is selected from the group consisting of hydrogen and $C^1$-$C_4$ alkyl; or a pharmaceutically acceptable salt or solvate thereof.

16. A method of claim 15 wherein the mammal is a human.

17. A method of claim 15 wherein the compound is a 5-HT$_{2A}$ selective compound.

18. A method for binding a 5-HT$_{2C}$ receptor in a mammal, comprising administering to the mammal a receptor-binding dose of a compound of Formula I

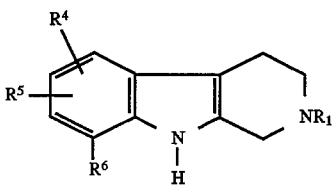

wherein:
- $R^1$ is hydrogen, $C_1$-$C_3$ alkyl, substituted $C_3$-$C_8$ cycloalkyl, $C_3$-$C_8$ cycloalkyl, $C_3$-$C_8$ cycloalkyl-($C_1$-$C_3$)alkyl, $C_5$-$C_8$ cycloalkenyl-($C_1$-$C_3$)alkyl, or $C_7$-$C_{16}$ arylalkyl;
- $R^4$ and $R^5$ are independently hydrogen, $C_1$-$C_3$ alkyl, $C_2$-$C_6$ alkenyl, halo, halo($C_1$-$C_6$)alkyl, halo($C_2$-$C_6$) alkenyl, $COR^7$, $C_1$-$C_{10}$ alkanoyl, $CO_2R^{7'}$, ($C_1$-$C_6$ alkyl)$_m$ amino, $NO_2$, —$SR^7$, $OR^7$, substituted $C_3$-$C_8$ cycloalkyl, $C_3$-$C_8$ cycloalkyl, $C_3$-$C8$ cycloalkyl-($C_1$-$C_3$)alkyl, $C_5$-$C_8$ cycloalkenyl-($C_1$-$C_3$)alkyl, or $C_7$-$C_{16}$ arylalkyl;
- m is 1 or 2;
- $R^7$ is hydrogen or $C_1$-$C_4$ alkyl;
- $R^{7'}$ is $C_1$-$C_4$ alkyl;
- $R^6$ is selected from the group consisting of $C_1$-$C_4$ alkyl, $OR^{5'}$, fluoro, bromo, iodo, and chloro; and
- $R^{5'}$ is selected from the group consisting of hydrogen and $C_1$-$C_4$ alkyl; or a pharmaceutically acceptable salt or solvate thereof.

19. A method of claim 18 wherein the mammal is a human.

20. A method of claim 18 wherein the compound is a 5-HT$_{2C}$ selectively compound.

21. A method for treating a mammal suffering from or susceptible to a condition associated with the modulation of a 5-HT$_{2A}$ receptor, comprising administering an effective amount of a compound of Formula I

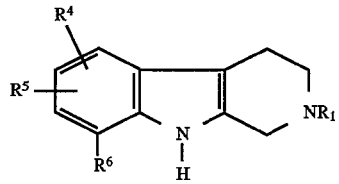

wherein:
- $R^l$ is hydrogen, $C_1$-$C_3$ alkyl, substituted $C_3$-$C_8$ cycloalkyl, $C_3$-$C_8$ cycloalkyl, $C_3$-$C_8$ cycloalkyl-($C_1$-$C_3$)alkyl, $C_5$-$C_8$ cycloalkenyl-($C_1$-$C_3$)alkyl, or $C_7$-$C_{16}$ arylalkyl;
- $R^4$ and $R^5$ are independently hydrogen, $C_1$-$C_3$ alkyl, $C_2$-$C_6$ alkenyl, halo, halo($C_1$-$C_6$)alkyl, halo($C_2$-$C_6$) alkenyl, $COR^7$, $C_1$-$C_{10}$ alkanoyl, $CO_2R^{7'}$, ($C_1$-$C_6$ alkyl)$_m$ amino, $NO_2$, —$SR^7$, $OR^7$, substituted $C_3$-$C_8$ cycloalkyl, $C_3$-$C_8$ cycloalkyl, $C_3$-$C_8$ cycloalkyl-($C_1$-$C_3$)alkyl, $C_5$-$C_8$ cycloalkenyl-($C_1$-$C_3$)alkyl, or $C_7$-$C_{16}$ arylalkyl;
- m is 1 or 2;
- $R^7$ is hydrogen or $C_1$-$C_4$ alkyl;
- $R^{7'}$ is $C_1$-$C_4$ alkyl;
- $R^6$ is selected from the group consisting of $C_1$-$C_4$ alkyl, $OR^{5'}$, fluoro, bromo, iodo, and chloro; and
- $R^{5'}$ is selected from the group consisting of hydrogen and $C_1$-$C_4$ alkyl; or a pharmaceutically acceptable salt or solvate thereof.

22. A method of claim 21 wherein the condition is anxiety and/or panic attacks.

23. A method for treating a mammal suffering from or susceptible to a condition associated with the modulation of a 5-HT$_{2C}$ receptor, comprising administering an effective amount of a compound of Formula I

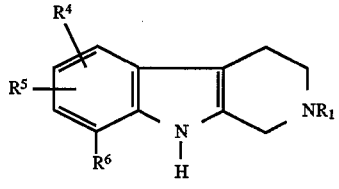

wherein:
- $R^1$ is hydrogen, $C_1$-$C_3$ alkyl, substituted $C_3$-$C_8$ cycloalkyl, $C_3$-$C_8$ cycloalkyl, $C_3$-$C_8$ cycloalkyl-($C_1$-$C_3$)alkyl, $C_5$-$C_8$ cycloalkenyl-($C_1$-$C_3$)alkyl, or $C_7$-$C_{16}$ arylalkyl;
- $R^4$ and $R^5$ are independently hydrogen, $C_1$-$C_3$ alkyl, $C_2$-$C_6$ alkenyl, halo, halo($C_1$-$C_6$)alkyl, halo($C_2$-$C_6$) alkenyl, $COR^7$, $C_1$-$C_{10}$ alkanoyl, $CO_2R^{7'}$, ($C_1$-$C_6$ alkyl)$_m$ amino, $NO_2$, —$SR^7$, $OR^7$, substituted $C_3$-$C_8$ cycloalkyl, $C_3$-$C_8$ cycloalkyl, $C_3$-$C_8$ cycloalkyl-($C_1$-$C_3$)alkyl, $C_5$-$C_8$ cycloalkenyl-($C_1$-$C_3$)alkyl, or $C_7$-$C_{16}$ arylalkyl;
- m is 1 or 2;
- $R^7$ is hydrogen or $C_1$-$C_4$ alkyl;
- $R^{7'}$ is $C_1$-$C_4$ alkyl;
- $R^6$ is selected from the group consisting of $C_1$-$C_4$ alkyl, $OR^{5'}$, fluoro, bromo, iodo, and chloro; and $R^{5'}$ is selected from the group consisting of hydrogen and $C_1$–$C_4$ alkyl; or a pharmaceutically acceptable salt or solvate thereof.

24. A method of claim 23 wherein the condition is a psychosis.

25. An article of manufacture comprising packaging material and one or more pharmaceutical agents contained within said packaging material, wherein one of said pharmaceutical agents is effective for the treatment of a condition associated with 5-$HT_{2C}$ modulation and is a compound of Formula I

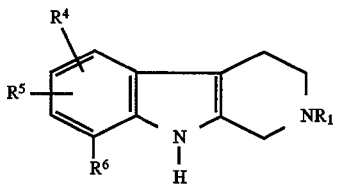

wherein:

$R^1$ is hydrogen, $C_1$–$C_3$ alkyl, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, or $C_7$–$C_{16}$ arylalkyl;

$R^4$ and $R^5$ are independently hydrogen, $C_1$–$C_3$ alkyl, $C_2$–$C_6$ alkenyl, halo, halo($C_1$–$C_6$)alkyl, halo($C_2$–$C_6$) alkenyl, $COR^7$, $C_1$–$C_{10}$ alkanoyl, $CO_2R^{7'}$, ($C_1$–$C_6$ alkyl)$_m$ amino, $NO_2$, —$SR^7$, $OR^7$, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, or $C_7$–$C_{16}$ arylalkyl;

m is 1 or 2;

$R^7$ is hydrogen or $C_1$–$C_4$ alkyl;

$R^{7'}$ is $C_1$–$C_4$ alkyl;

$R^6$ is selected from the group consisting of $C_1$–$C_4$ alkyl, $OR^{5'}$, fluoro, bromo, iodo, and chloro; and $R^{5'}$ is selected from the group consisting of hydrogen and $C_1$–$C_4$ alkyl; or a pharmaceutically acceptable salt or solvate thereof; and said packaging material comprises a label which indicates that said pharmaceutical agent can be used for the treatment of a condition associated with 5-$HT_{2C}$ modulation.

* * * * *